United States Patent [19]

White et al.

[11] Patent Number: 5,732,706
[45] Date of Patent: Mar. 31, 1998

[54] ULTRASONIC ARRAY WITH ATTENUATING ELECTRICAL INTERCONNECTS

[75] Inventors: Timothy E. White; Neal R. Butler, both of Acton; Marcus Hatch, Waltham; Kenneth R. Erikson, Lexington; Curtis A. Vock, Salem; Wayne C. Haase, Acton; Michael A. Martinelli, Winchester, all of Mass.

[73] Assignee: Lockheed Martin IR Imaging Systems, Inc., Lexington, Mass.

[21] Appl. No.: 621,104

[22] Filed: Mar. 22, 1996

[51] Int. Cl.⁶ ................................................ A61B 8/00
[52] U.S. Cl. ........................................ 128/661.01; 73/626
[58] Field of Search .......................... 128/660.07, 661.01, 128/662.03, 663.01; 73/625, 626; 364/413.25; 310/328, 334, 335, 336, 348

[56] References Cited

U.S. PATENT DOCUMENTS

| | | |
|---|---|---|
| 3,958,559 | 5/1976 | Glenn et al. . |
| 4,183,249 | 1/1980 | Anderson . |
| 4,211,948 | 7/1980 | Smith et al. . |
| 4,211,949 | 7/1980 | Brisken et al. . |
| 4,224,829 | 9/1980 | Kawabuchi et al. . |
| 4,262,399 | 4/1981 | Cady . |
| 4,277,711 | 7/1981 | Hanafy . |
| 4,420,707 | 12/1983 | VanValkenburg . |
| 4,432,007 | 2/1984 | Cady . |
| 4,506,550 | 3/1985 | Sandhu . |
| 4,543,829 | 10/1985 | Lerch . |
| 4,608,868 | 9/1986 | Green . |
| 4,674,514 | 6/1987 | Abbott et al. . |
| 4,694,434 | 9/1987 | von Ramm et al. . |
| 4,737,921 | 4/1988 | Goldwasser et al. . |
| 4,836,026 | 6/1989 | P'an et al. . |
| 4,852,577 | 8/1989 | Smith et al. . |
| 4,880,010 | 11/1989 | Szilard . |
| 4,905,202 | 2/1990 | Robillard . |
| 4,908,774 | 3/1990 | Lund et al. . |
| 4,989,143 | 1/1991 | O'Donnell et al. ............ 128/661.01 |
| 5,083,567 | 1/1992 | Uchibori . |
| 5,090,609 | 2/1992 | Nakao et al. . |
| 5,119,342 | 6/1992 | Harrison, Jr. et al. . |
| 5,121,361 | 6/1992 | Harrison, Jr. et al. . |
| 5,121,364 | 6/1992 | O'Donnell . |
| 5,140,558 | 8/1992 | Harrison, Jr. et al. . |
| 5,142,649 | 8/1992 | O'Donnell . |
| 5,172,343 | 12/1992 | O'Donnell . |
| 5,203,335 | 4/1993 | Noujaim et al. . |
| 5,230,340 | 7/1993 | Rhyne . |
| 5,235,982 | 8/1993 | O'Donnell . |
| 5,311,095 | 5/1994 | Smith et al. . |
| 5,331,964 | 7/1994 | Trahey et al. ............ 128/661.01 |
| 5,347,086 | 9/1994 | Potter et al. . |
| 5,483,963 | 1/1996 | Butler et al. . |

OTHER PUBLICATIONS

W.N. McDicken, "Diagnostic Ultrasonics: Principles and Use of Instruments", Third Edition, Churchill Livingstone, 1991, pp. 216, 305–306.

K.R. Erikson et al., "Integrated Acoustic Array", *Acoustical Holography.*, vol. 7, 1977, pp. 423–444.

*Primary Examiner*—George Manuel
*Attorney, Agent, or Firm*—Hans I. Sun; Emil Moffa

[57] ABSTRACT

An array of ultrasonic transducers, where each of the ultrasonic transducers has a matching layer end and a driving layer/individually isolated end. A bump bond connects each one of the ultrasonic transducers to a substrate. A high voltage electrical conductor is connected to at least one driving layer/individually isolated end to provide a drive signal to at least one of the ultrasonic transducers. A conductive/matching layer is disposed to electrically connect each matching layer end. An outer matching layer is connected to the conductive/matching layer. The bump bond is an indium or solder bump bond having a contact area for contact with an ultrasonic transducer less than 20 percent of the driving layer/individually isolated end for the contacted ultrasonic transducer so as to provide mechanical stability while reducing cross talk among the plurality of ultrasonic transducers.

28 Claims, 13 Drawing Sheets

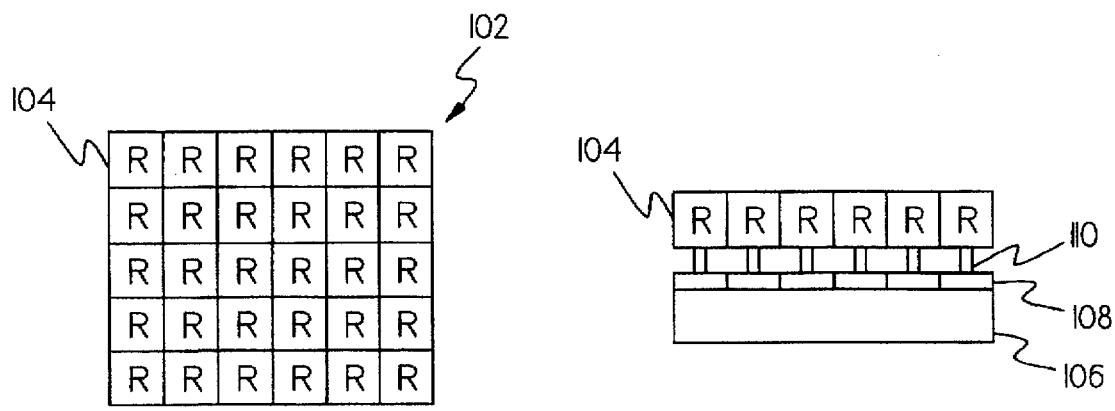
_Fig_ 2A    _Fig_ 2B
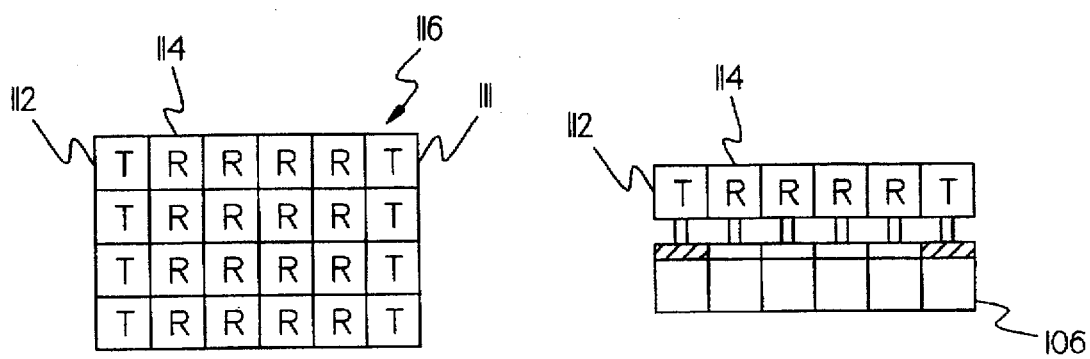
_Fig_ 3A    _Fig_ 3B

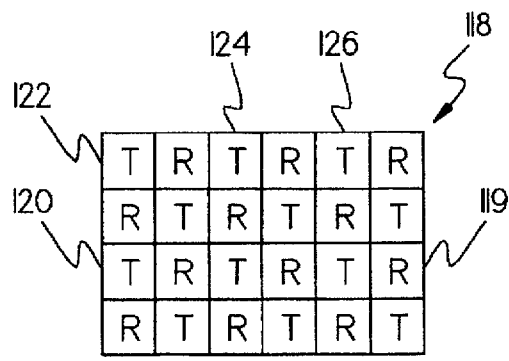
_Fig_- 4
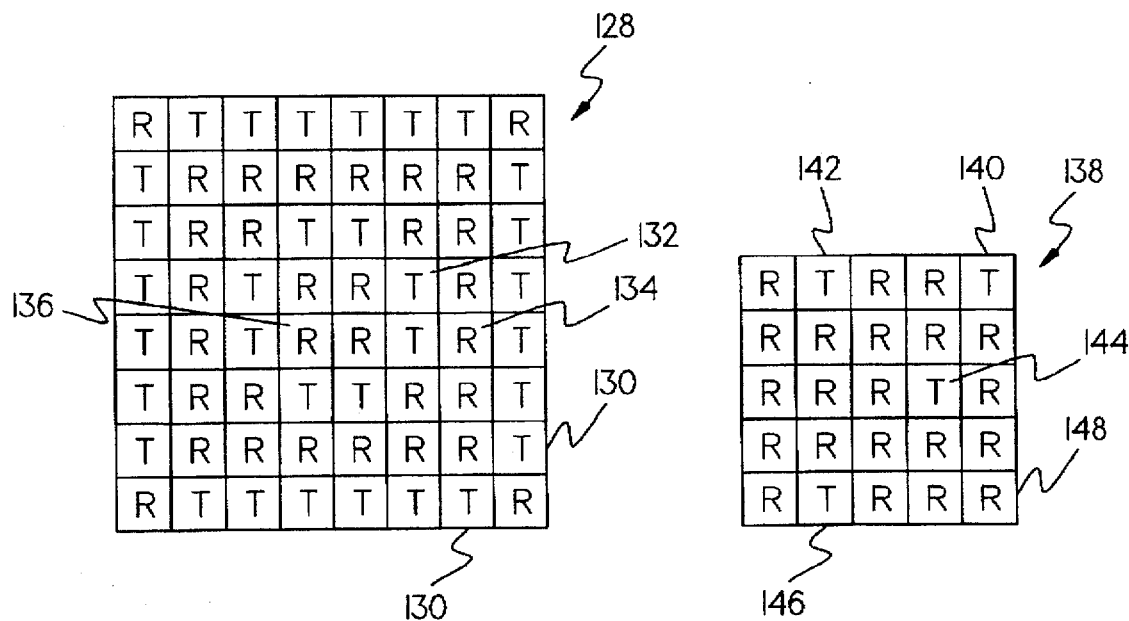
_Fig_- 5
_Fig_- 6

ULTRASONIC ARRAY WITH ATTENUATING ELECTRICAL INTERCONNECTS

The invention relates to an ultrasound imaging array and, more particularly, to an ultrasound imaging array with attenuating electrical interconnects.

BACKGROUND OF THE INVENTION

Ultrasonic sensors are used in a wide range of applications, particularly medical imaging. Acoustic arrays configured as a two dimensional array of sensors using integrated circuit technology have been developed. One such acoustic array, for example is disclosed in U.S. Pat. No. 5,483,963 to Butler et al., issued Jan. 16, 1996, wherein certain rights have been assigned to the assignee of the instant application. U.S. Pat. No. 5,483,963 is incorporated herein by reference. Butler et al. disclose a plurality of ultrasonic transducers arranged in a reticulated two dimensional array, each sensor having a first independent electrical connection, and each sensor having a second common electrical connection. An integrated circuit signal processing means for processing signals from the two dimensional array of ultrasonic transducers is connected to each one of the plurality of ultrasonic transducers at the first independent electrical connection.

While known ultrasonic systems are useful, their operation is sometimes impeded by cross talk interference transmitted from one ultrasonic transducer to another. Therefore, it is a motivation of the present invention to provide a novel means for reducing such deleterious effects from cross talk.

Further, transmitter elements in an ultrasonic system require relatively high voltage. Therefore, known ultrasonic arrays comprise circuitry capable of operating under high voltage conditions. The use of such relatively high voltage precludes constructing electronic integrated circuits to operate both receiver and transmitter elements with, for example, low voltage CMOS integrated circuit technology. CMOS has inherent advantages of relatively small size and low power. Therefore, it is another motivation of the present invention to provide an ultrasonic system having transmitter and receiver array electronics comprised of low voltage integrated circuits.

SUMMARY OF THE INVENTION

The present invention provides an ultrasonic array comprising a plurality of ultrasonic transducers, where each of the plurality of ultrasonic transducers has a matching layer common electrode end and an isolated end. A bump bond connects each one of the ultrasonic transducers' isolated ends to a substrate where the bump bond is constructed so as to provide mechanical stability while reducing cross talk among the plurality of ultrasonic transducers. In a transmit array, a high voltage electrical conductor is connected to at least one isolated end to provide a drive signal to at least one of the ultrasonic transducers. A conductive layer is disposed to electrically connect each matching layer end. An outer matching layer or layers is connected to the conductive layer.

In one aspect of the invention, the bump bond comprises an indium bump bond having a contact area for contact with an ultrasonic transducer in the range of less than 20 percent of the area of the isolated layer end for the contacted ultrasonic transducer so as to provide electrical contact, and mechanical stability while reducing cross talk among the plurality of ultrasonic transducers.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

To illustrate this invention, a preferred embodiment will be described herein with reference to the accompanying drawings.

FIG. 2A and FIG. 2B schematically illustrate a top view and a side view, respectively, of a pattern of a receiver array.

FIG. 3A and FIG. 3B schematically illustrate a top view and a side view, respectively, of a pattern of a transducer array comprising transmit and receive elements made in accordance with one aspect of the present invention.

FIG. 4, FIG. 5 and FIG. 6 schematically illustrate patterns of further examples of transducer arrays comprising transmit and receive elements made in accordance with alternate embodiments of the present invention.

DETAILED DESCRIPTION OF THE PREFERRED EMBODIMENT

Figure 1:
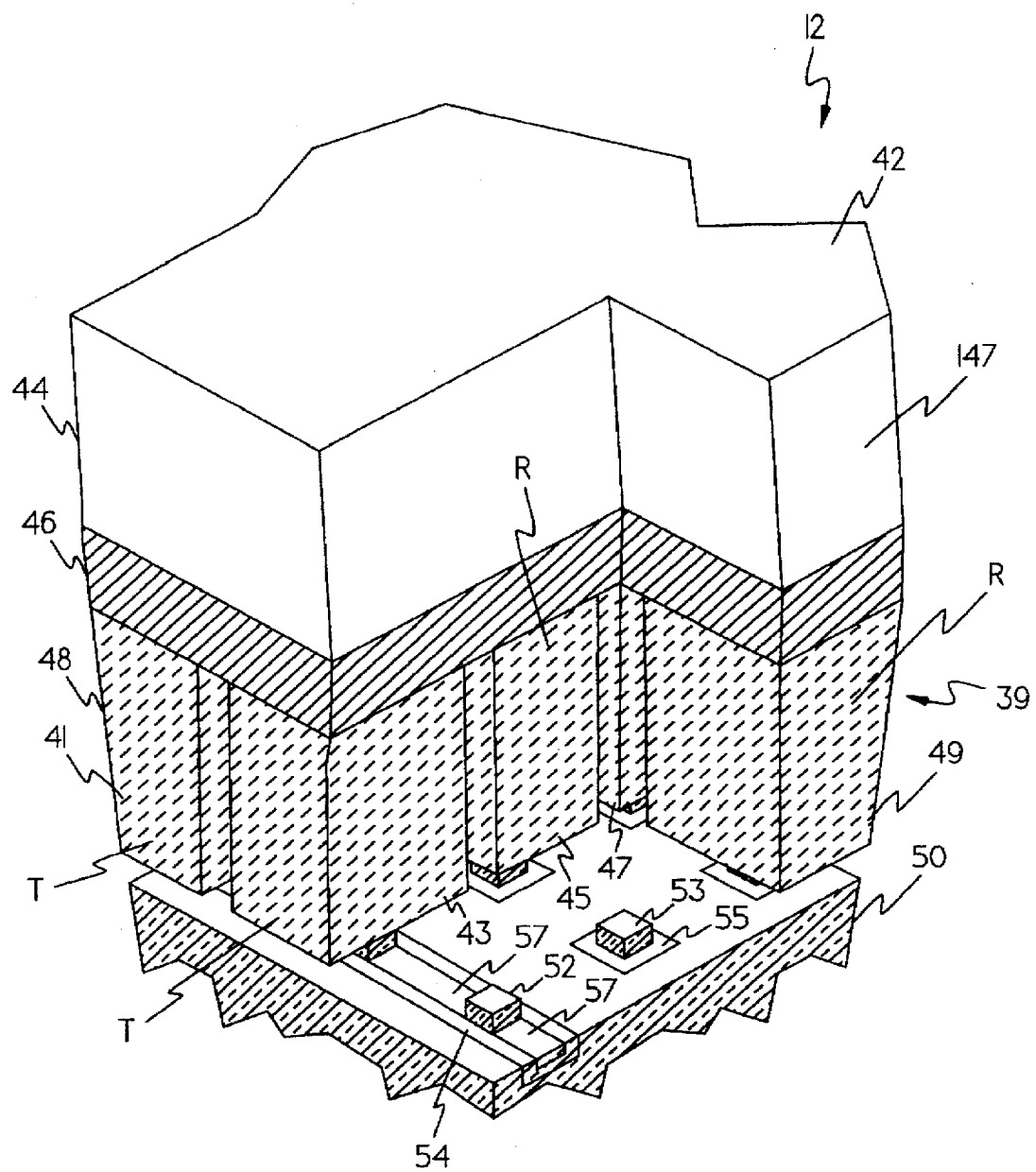
FIG. 1 shows an isometric drawing of a portion of an ultrasonic array and an integrated circuit made in accordance with one aspect of the present invention.

Refer now to FIG. 1, FIG. 1 shows a schematic isometric drawing of a portion of an ultrasonic array and an integrated circuit made in accordance with one aspect of the present invention. The ultrasonic array comprises a plurality of piezoelectric transducer elements, or "piezels", 41, 43, 45, 47 and 49. The piezoelectric transducer elements include interspersed transmitter elements T (such as elements 41 and 43) and receiver elements R (such as elements 45, 47 and 49). Each transducer element, or piezel, 41, 43, 45, 47 and 49 comprises ultrasonic transduction material, such as a suitable composite piezoelectric material known in the art. Indium bumps 52 and 53 bond each receiver element R to an integrated circuit, such as CMOS VLSI integrated circuit 55. Insulation material 54 insulates each transmitter element T from the CMOS VLSI integrated circuit 55. Selected rows or groupings of transmitter elements may advantageously be connected by, for example, high voltage conductor paths 57 wherein the high voltage conductor paths 57 are laid over the insulation material 54 insulating the high voltage conductor paths 57 from semiconductor substrate 50. In the case of a traditional CMOS VLSI circuit, the insulation material 54 may be the same as the circuit passivation layer. Alternatively, an insulated metal line within the circuit may, or may not, in turn, be covered with an insulator. It will be understood that a plurality of such high voltage conductor paths 57 may be similarly constructed for connecting transmitter elements throughout an array of elements. High voltage conductor path 57 may advantageously be connected to other similar high voltage conductor paths and to external transmission circuitry (not shown) of conventional design. As a matter of design choice, the high voltage conductor paths may be joined together or separately connected to the external transmission circuitry to enable phasing of transmit elements.

Acoustic array 12 optionally comprises a protective seal and cover with an outer matching layer 44, one or more matching layers 147 and a common electrically conductive electrode 46. By matching the acoustic impedance of the piezoelectric detector 48 with that of body tissue through the use of matching layers 44 and 147 transducer sensitivity increases sharply. The outer matching layer 44 may comprise an acoustic material or composite material having an acoustic impedance suitable for coupling of energy to the transducer elements. Plastic or tungsten-loaded araldite has been used to make quarter wave matching layers. See *Diagnostic Ultrasonics: Principles and Use of Instruments* by W. M. McDicken (1991). The common electrode 46 may comprise a thinner layer of a conductor, such as gold or nickel, for example, for contact to the piezoelectric layer 48.

The individual receiver piezels 45, 47 and 49 may be advantageously hybridized onto the silicon read out IC (ROIC) 55. A saw cut reticulation has been made completely through the ceramic PZT layer 48 up to the common electrode 46. By cutting all the way through the PZT layer 48, electrical and mechanical cross talk can be reduced thereby improving the resolution of the directed beam, as well as the sensitivity to the received signal. Cutting of the transducer material 48 through to the common electrode 46 increases inter-element isolation. Furthermore, by using air in between the piezels 41, 43, 45, 47 and 49 as an acoustical insulator, acoustic cross talk can be reduced significantly as well. Air isolation between elements, or a filler material such as epoxy, silicone, plastic or other equivalent materials embedded between elements can significantly reduce cross talk in both directions thus improving system resolution.

It is well known that sub-reticulation within an element may be also used to create a composite detector. The special structure of the device of the invention is particularly well suited for fabrication of two dimensional arrays because the tops of the transducers are connected by the common electrode 46 and matching layers and the other side is connected via the bump bond to the multiplexer.

Figure 21:
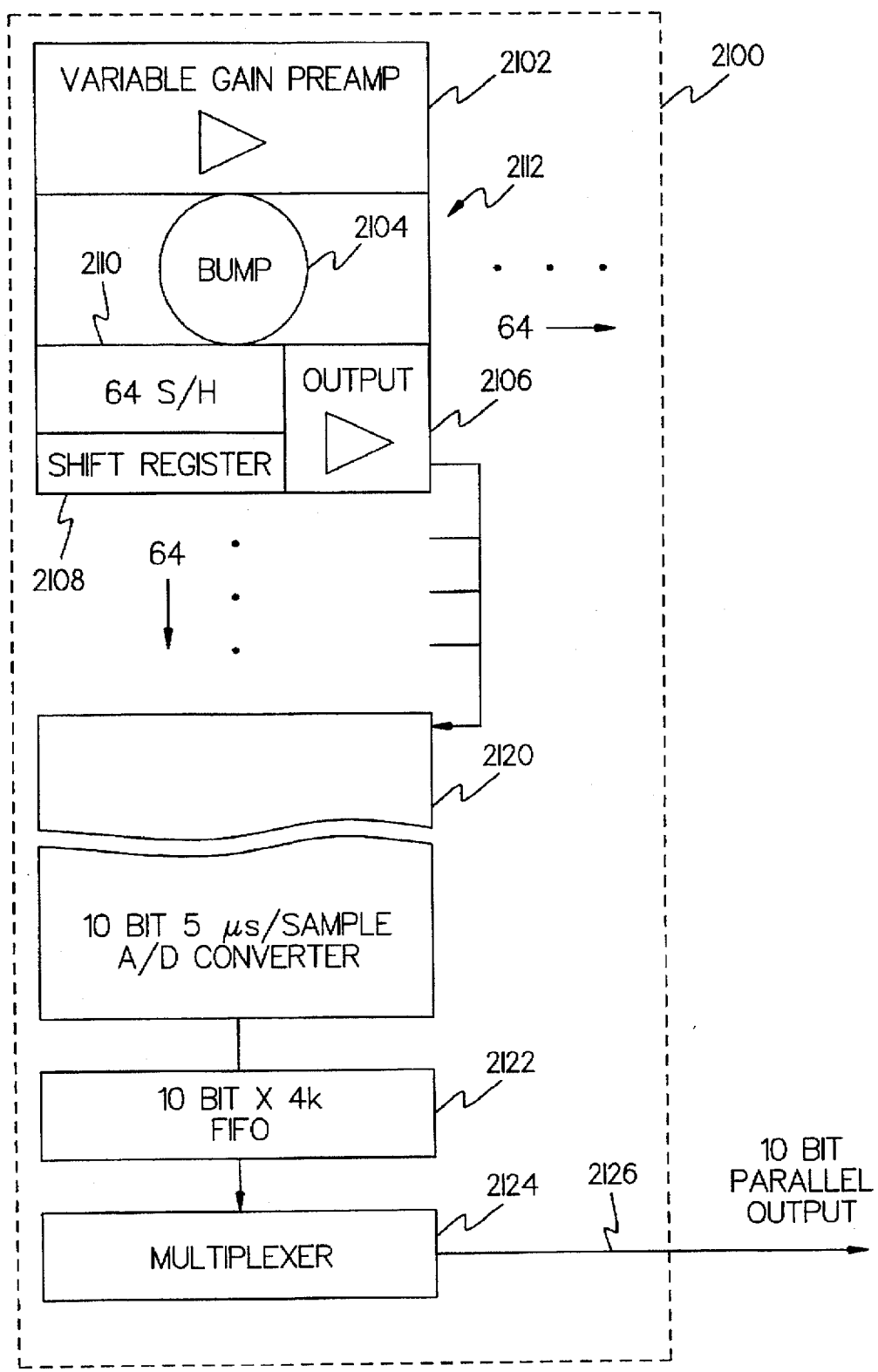
FIG. 21 schematically illustrates one embodiment of on-chip electronic circuitry incorporating an analog-to-digital converter constructed on an integrated circuit employed in one aspect of the invention.

Additional available space on the active surface of the semiconductor allows the integration of other active electronic circuitry, such as pre-amps, sample holds, peak detectors and an on-chip analog-to-digital converter. The integrated analog-to-digital converter as illustrated in FIG. 21 would have the following advantages: reduced power, improved transmission of signals over the cables, and reduced conversion rates by performing analog to digital conversion before multiplexing rather than after signal multiplexing.

FIG. 2A and FIG. 2B schematically illustrate a top view and a side view, respectively, of a pattern of a receiver array, wherein each of the transducers in the array function to receive signals. In one example of such a configuration a separate array of transmitters (not shown) may be employed to transmit signals. In another example of such a configuration receiver and transmitter functions may be switched using the same elements but applying different control signals as discussed hereinbelow with reference to FIG. 15. In the aforementioned switched configuration, relatively higher voltage DMOS circuitry, instead of CMOS circuitry, may be employed to carry out the functions of ROIC 55. Ultrasound imagery as traditionally constructed requires transmission of a single pulse and then "listening" to returning echoes. An image is then constructed from the varying time-dependent intensity of the returned signal. The array permits the sampling and storage for each element directly behind each element. The amount of signal processing and sample storage in the ROIC is limited only by conventional circuit design rules.

Figure 7:
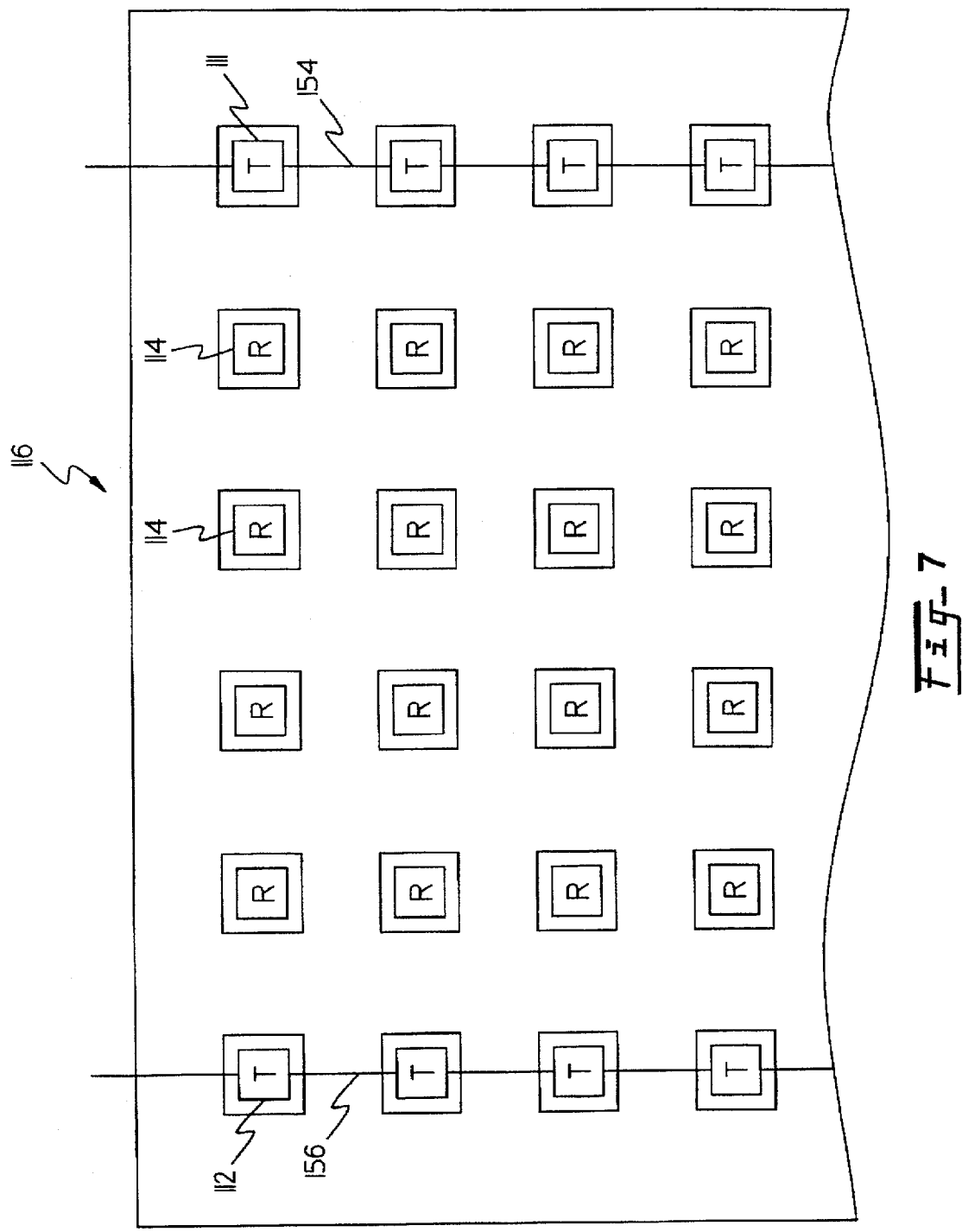
FIG. 7, FIG. 8 and FIG. 9 schematically show example patterns of further examples of transducer arrays comprising transmit and receive elements using a high voltage circuit path to connect selected transmitter elements.

FIG. 3A and FIG. 3B schematically show an array 116 of receivers 114 and two linear arrays of transmitters 112. FIG. 3A shows a top view of the array 116 and FIG. 3B shows a side view of the array 116. FIG. 7 shows power routing for the transmitter arrays of FIGS. 3A and 3B. High voltage and control line 156 is connected to each transmitter 112 in the linear array 116. Similarly, high voltage and control line 154 connects each transmitter in linear array 111. Independent high voltage and control lines 154 and 156 provide independent switching of linear arrays. The multiple transmit elements may advantageously be wired to be pulsed simultaneously or pulsed in groups permitting transmit beam-forming as in conventional ultrasound. Use of the high voltage and control lines 154, 156 enables the transmission of relatively high voltage signals to the transmission elements from an external transmission circuit wherein the external transmission circuit may be of a conventional design. Thus, since the transmission circuitry may be implemented externally, the ROIC comprise relatively lower voltage CMOS, therefore, the circuitry can be very dense. Thus, the apparatus of the invention allows increased signal processing and/or time sampling to take place in the ROIC. As a result, significant parallel signal processing may be implemented using CMOS circuitry in accordance with known practices.

Figure 8:
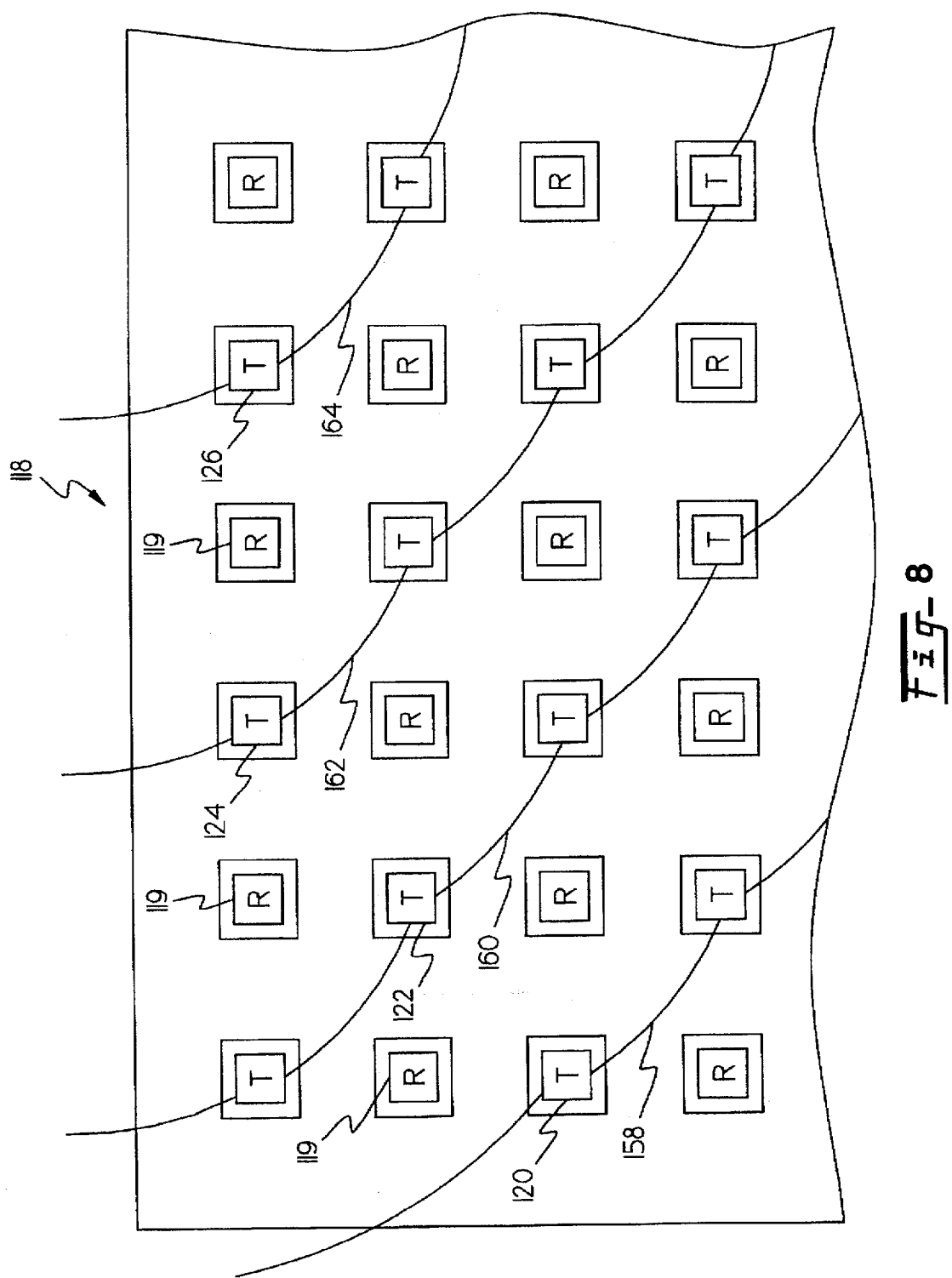

FIG. 4 schematically shows an array 118 of receivers 119 and four linear arrays of transmitters 120, 122, 124 and 126. Transmitters 120, 122, 124 and 126 are positioned in a diagonal configuration. FIG. 8 shows power routing for the transmitter arrays of FIG. 4. High power line 158 is connected to each transmitter in linear array 120. Similarly, high power line 160 connects each transmitter in linear array 122. High power line 162 connects each transmitter in linear array 124 and high power line 164 connects each transmitter in linear array 126. As in the configuration of FIG. 7 independent high power lines provide independent switching of linear arrays 154 and 156.

Figure 9:
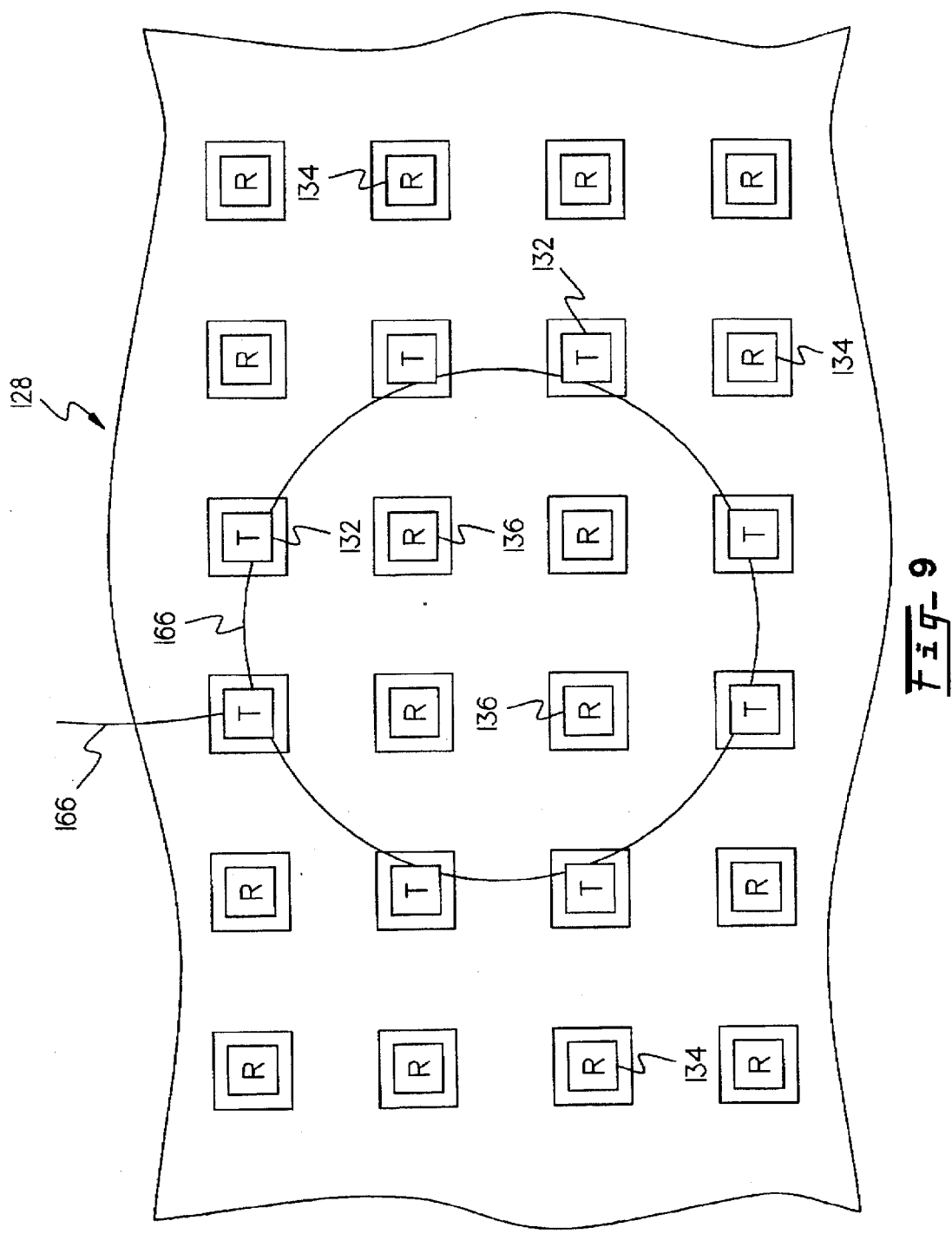

FIG. 5 schematically shows an array 128 of receivers 134 and transmitters 132. The transmitters 132 are configured as generally circular 130 and 136. FIG. 9 shows a generally circular arrangement of transmitters 132 among receivers 134. High voltage and control line 166 is connected to each transmitter in generally circular arrangement of transmitters 132. Outer circular arrangements of transmitters are provided with separate switching lines to provide independent activation of each set of transmitters.

FIG. 6 schematically shows an array 138 of receivers 148 and a predetermined pattern of transmitters 140, 142, 144 and 146. Independent high voltage and control lines may be connected to each transmitter independently or each transmitter may be connected by a single high power supply line.

As discussed above with respect to, for example, FIG. 3A, in one embodiment of the invention the arrays are built with low voltage CMOS. Use of CMOS, as compared to other circuit technologies, allows miniaturization that permits dynamic electronic focus in both directions using cell based logic and circuitry. A form of such dynamic electronic focusing is known in the field of phased array radar, but was previously limited in ultrasound to steering the beam in one direction only such as in transmit only, receive only, or both. The two dimensional array with active circuitry directly behind each element makes possible focusing or steering the beam in both directions. The result of such focusing and steering is a sharper picture and/or increased flexibility.

Figure 10:
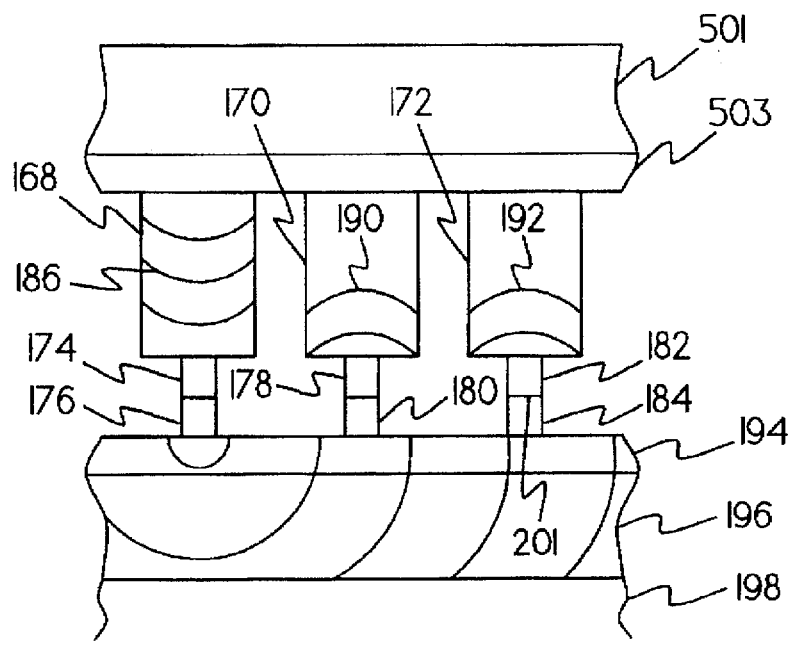
FIG. 10 illustrates cross talk properties in an ultrasonic array.

FIG. 10 illustrates the effect of signal cross talk. Signal cross talk is generated by the operation of one piezel affecting other elements of the array. Element 168, connected by indium bump bond 174 to bump bond 176 connects to active device layer 194. Active layer 194 is deposited on semiconductor substrate 196. Ultrasonic element 168 receives or transmits signal 186. Signal 186 is shown as a wave train that propagates to the other array elements such as transducer elements 170 and 172. Active layer 194 and substrate 196 act to transmit waves or portions of waves 188 of the signal 186 though indium bump bonds 180 and 178 to element 170. Cross talk generates wave train 190 in piezel 170. Active layer 196 and substrate 194 act to transmit waves 188 of signal 186 though indium bump bonds 184 and 182 to element 172. Cross talk generates wave train 192 in piezel 172.

The size of the bump interconnections 182 and 184, 178 and 180, 174 and 176 is particularly significant in controlling the acoustic properties of the back surface of the transducer 168, 170 and 172 and thus also the cross talk resulting from acoustic energy received or transmitted by one element that subsequently influences another neighboring element. Ideally, transducer elements would be completely isolated. If such were the case then energy impinging on, or transmitted by, one element would have no effect on its neighbors and each element would be independent. Air is an excellent isolator for ultrasound but, without the structure of the present invention, there has not been a means to approach the ideal case. Prior to the present invention, problems associated with reducing cross talk were in the physical implementation of the transducer array structure. In order to sense the electrical energy in the transducer there must be either a hard electrical connection or an extremely efficient and precisely impedance-matched capacitive coupling established. Historically, structures employed have been constrained for fabrication purposes to being held together with appropriate attenuating or reflecting adhesives and glues to absorbing conductive substrates. In contrast to previously known structures, the new structure of the present invention approximates the ideal case. The top surface is connected only by the common electrode 503 which is incorporated into the matching layer 501. The bottom of the transducer 192 is only contacted by bump 182. The sides are isolated by air or other material as discussed above to improve mechanical stability. If the bump 182 is maintained at a size which is small with respect to the element end area, cross talk transmitted by the bump becomes insignificant and can be ignored. It has been found that maintaining the bump size less than about 10–20% of the size of the piezel contact area appears from electrical models to be the critical point where the size effect is most significant. This is a direct function of bump area with respect to element area.

The primary effects from any mechanical connection which are undesirable are: (a) conduction of the ultrasound energy into the mounting surface where it would be re-radiated and detected at the neighboring elements; and (b) constraint of the transducer material by the contact which would prevent the full piezoelectric response. Of these two effects, the first is the larger and more deleterious but both are reduced by small contacts. If the bump required the full area, then the amount of energy transferred into the substrate would only be a function of the acoustic properties of the bump material with respect to the transducer material and the substrate. For the simplified case of no attenuation by the bump, all energy falling on each element would be re-radiated to its neighbors with only the attenuating properties of the substrate to control it. However, if the bump is small, it will act as an attenuator because only the area fraction occupied by the bump will conduct the energy. Thus, with a 10% area fraction, only 10% of the energy will be conducted into the substrate. To be sensed by a neighbor, the energy must pass through a second 10% attenuator and thus reduced by another factor of ten. The result would be 1% cross talk, 99% attenuation, if the bump and substrate had no attenuating properties. If the bump area were reduced to 5%, a 0.25% cross talk, 99.75% attenuation, would result.

This effect is independent of the substrate so it would be equally applicable for traditional transducers and substrates including, but not limited to, read out integrated circuits. It permits electrical contact to the isolated side of a transducer without adding a significantly acoustically conductive path.

Figure 11:
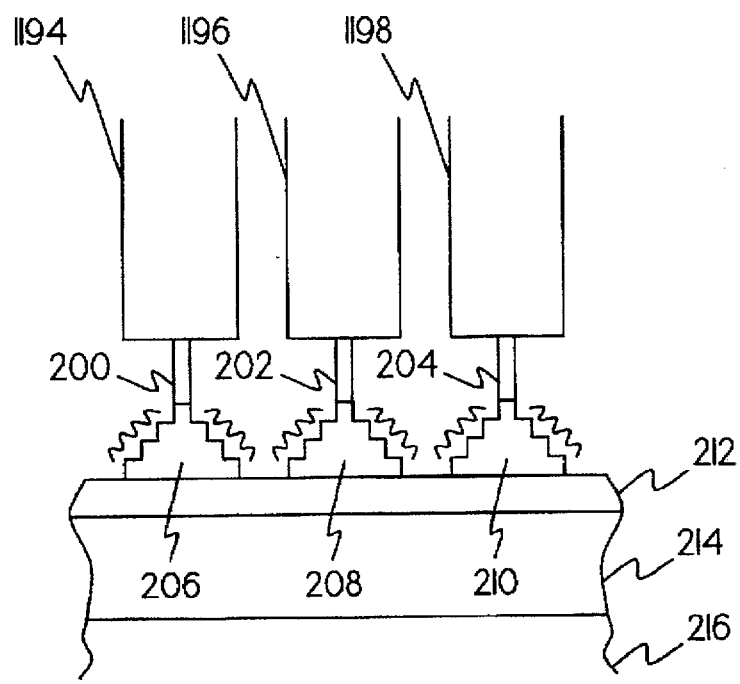
FIG. 11 schematically illustrates a cut away side view of an alternate embodiment of the bump bonding features of the invention.

FIG. 11 shows one alternate aspect of the invention to reduce signal cross talk. Small indium bumps 200, 202 and 204 connect transducer elements 1194, 1196 and 1198 to stepped bond connectors 206, 208 and 210, respectively. Stepped bond connectors 206, 208 and 210 and bumps 200, 202 and 204 are surrounded by an electrically insulating material such as air, one of many known epoxies or silicone based materials. Filler material, if desired, can be injected into the gap around the bump bonds to provide stabilization. Selection of the filler material may be based upon acoustical and electrical impedance to minimize cross talk. The graded structure of the stepped bond connectors permits the tailoring of the acoustic properties of the interconnection layer 212 between the piezoelectric elements and the mounting substrate 214. By adjusting the area and volume fractions of the electrical connections, the acoustic properties of the interconnection layer can be adjusted.

Figure 12:
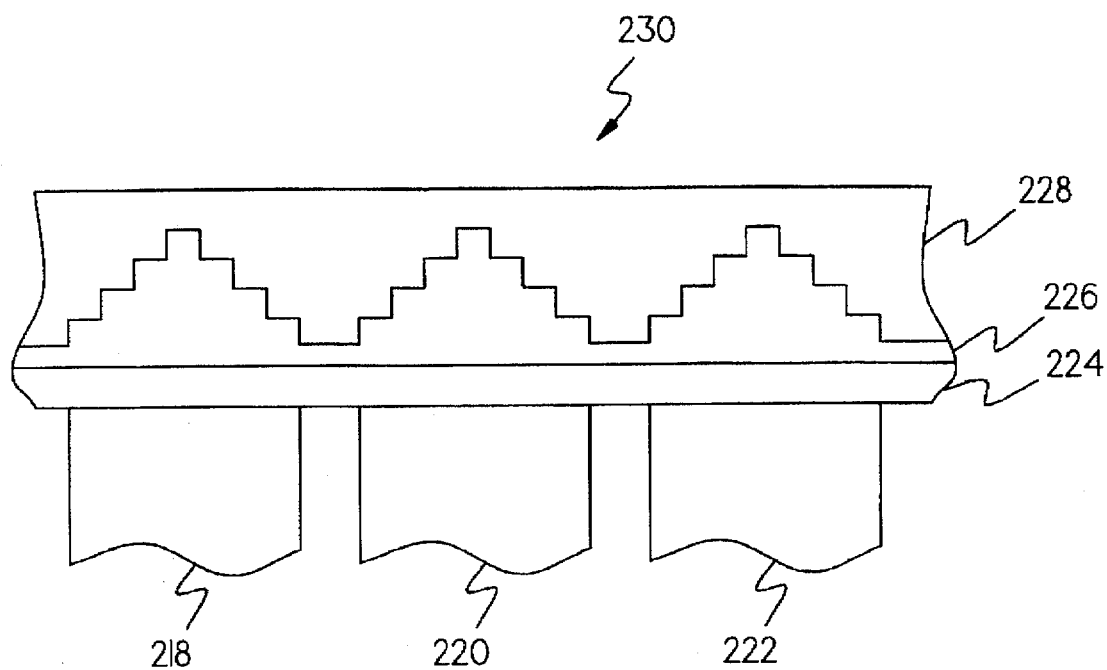
FIG. 12 illustrates a further alternate embodiment of a matching layer.

FIG. 12 shows a cross section of a stepped matching layer for array 230. Common electrode 224 is connected to matching layer 1 226 which on one side is flat and the other is configured in a step arrangement. Matching layer 2 228 has a matching step arrangement. Transducers 218, 220 and 222 are connected in the fashion of FIG. 1 to common electrode 224. The stepped matching layers act to dampen cross talk signals generated by transducers 218, 220 and 222. The step sizes in matching layers 226 and 228 are selected to be small with respect to the wavelengths of the ultrasound.

Figure 13:
FIG. 13 schematically shows an example of an ultrasonic lens.
Figure 14:
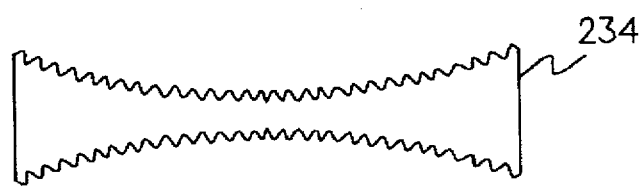
FIG. 14 schematically shows an example of a matching layer created in the surface of the lens.

FIG. 13 shows a concave lens of the invention and FIG. 14 shows a serrated concave lens of the invention. The prior art is constrained to select materials which have the desired acoustic properties as intrinsic properties. As contemplated by the present invention, desired material properties may be constructed from two different materials. Surface finish geometries of lateral area and thickness may advantageously be selected to be significantly less than a wavelength in order to reduce diffraction effects. In the simplest case, if graded material properties were to be constructed, binary optic structures might be used to make a graded interface where one side of the interface fully comprised a first material, the other side was an entirely different material and the intervening layers were different area fractions of the two materials. This could be expanded to have multiple materials in the stack to yield multiple variable properties. Or, if there was no material with the correct initial properties, such a graded or sloped structure could be constructed from two different materials applied in the proper area percentage to obtain the correct average properties.

Some experimental evidence in support of this approach is available. Lenses were fabricated by Loral Infrared and Imaging Systems, Inc. of Lexington Mass., U.S.A. The lenses are relatively rough but, because the roughness is less than wavelength dimensions, there is little or no effect, as evidenced by an excellent nearly theoretical performance of the lens. In another example of a matching layer, a lens having an inherent surface roughness may be used in the above type of structure in the lens surface. The surface may advantageously be immersed in fluid that fills any open space between the lens and the transducer array, thereby creating an inherently graded matching, anti-reflection surface without a coating. Creating such a graded lens surface may be done using any suitable known process such as, for example, machining, molding, or any method of material deposition. The possibility of molding in ridges is particularly attractive since it would require no additional steps to create a graded matching surface. Furthermore, the approach, because it incorporates the fluid surrounding the lens, is inherently self correcting if the fluid properties change significantly.

Figure 15:
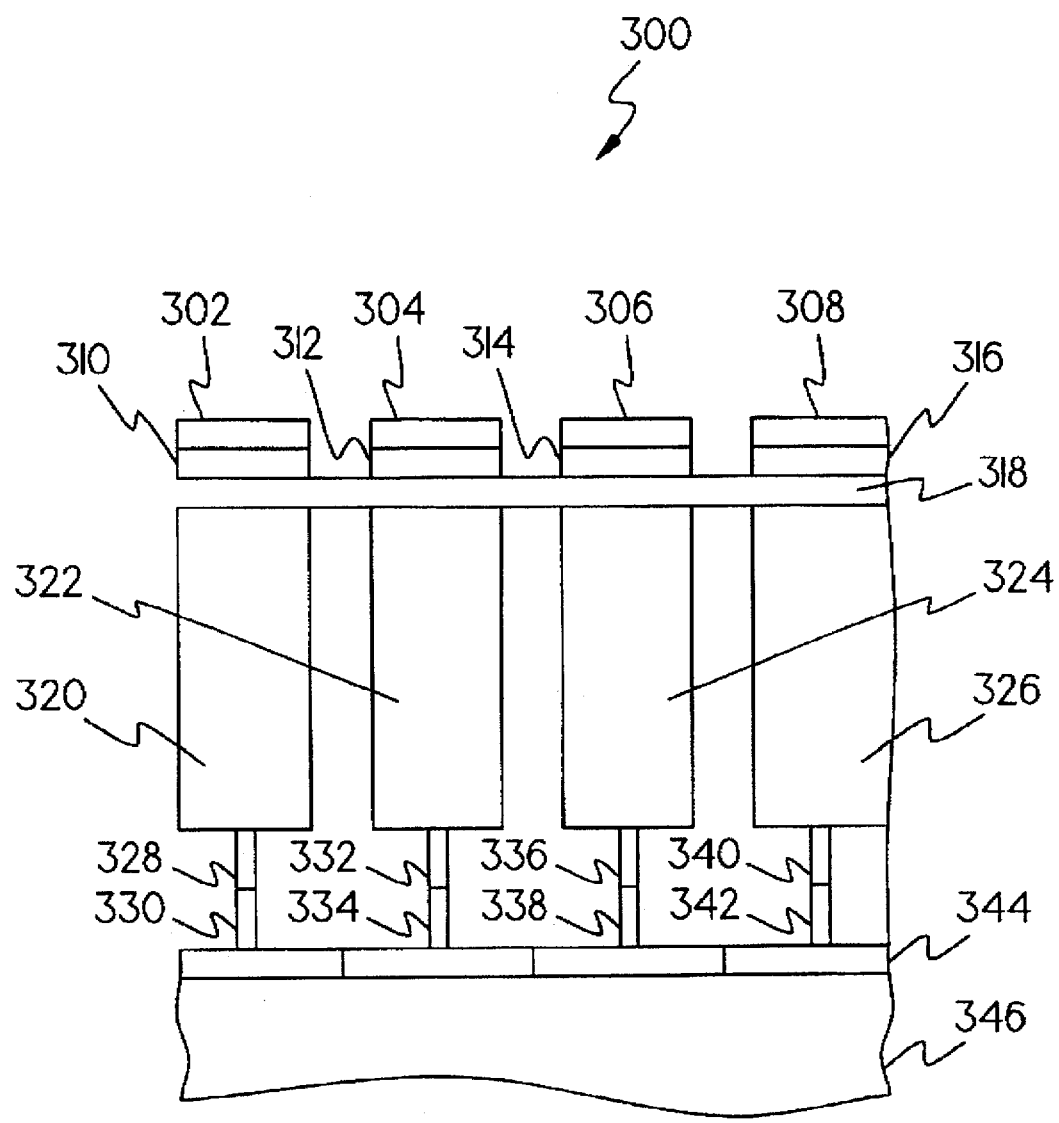
FIG. 15 schematically shows a cut away view of a partial ultrasonic array made in accordance with one aspect of the present invention.

FIG. 15 shows an alternate embodiment of the invention including an array of transducers 300. Cross talk is reduced in the configuration of FIG. 15 by isolating upper and lower matching layers by cutting in between the matching layers for each transducer. Common electrode 318 serves to connect one side of the transducer array. Transducers 320, 322, 324 and 326 may advantageously be indium bump bonded to active layer 344. It is believed that full reticulation of the upper and lower matching layers, up to the common electrode 318, results in better signal coupling and better isolation between elements.

Figure 16:
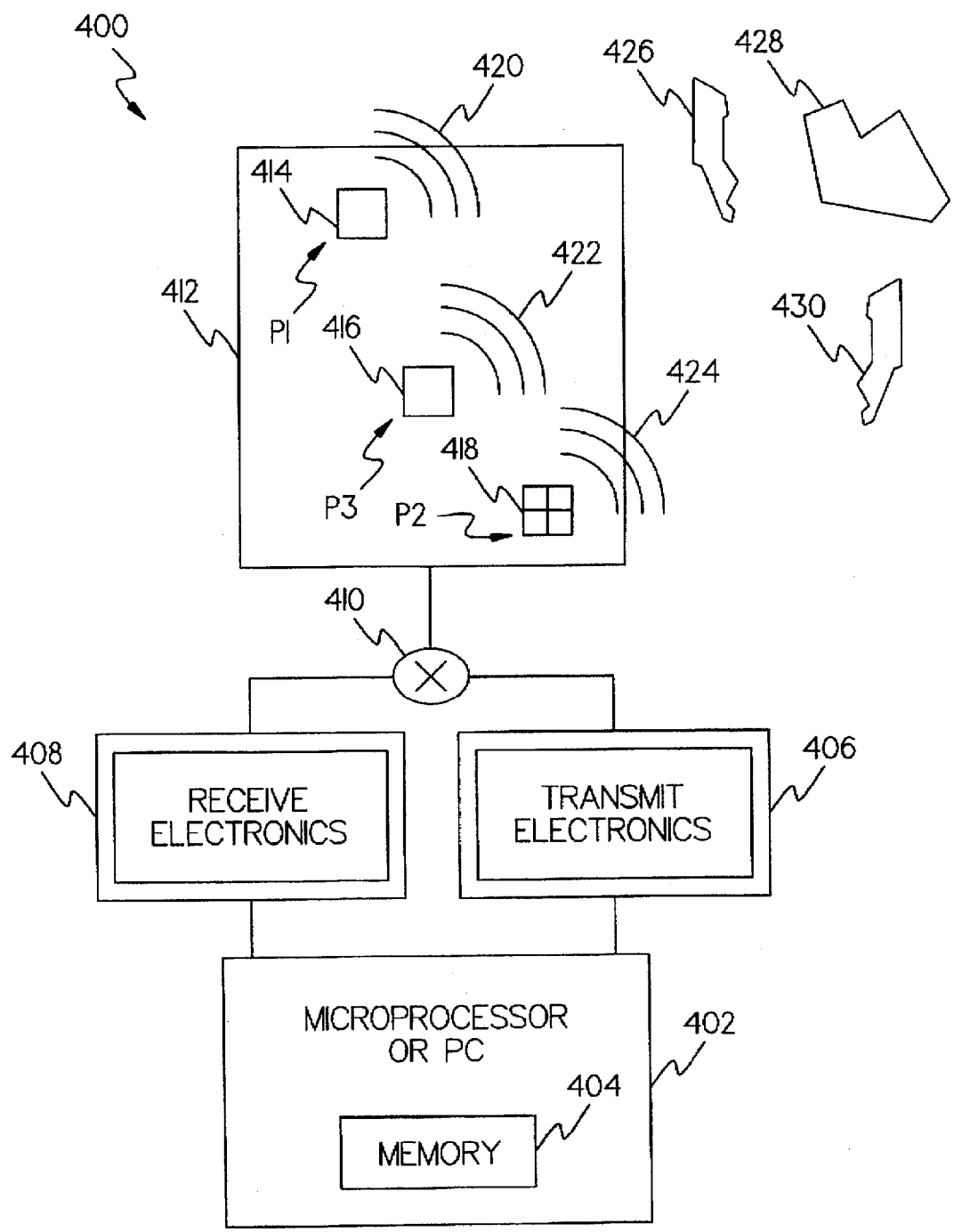
FIG. 16 shows a schematic of an ultrasonic array and system of the invention imaging a target.

FIG. 16 shows a schematic of the array 412 of the invention imaging a target 428. Piezoelectric array 412 comprises a plurality of piezels represented by piezels 414, 416 and 418. Alternately, FIG. 16 could function in a bistatic mode with separate transmit and receive transducers but with similar microprocessor or PC monitoring, control and selection of any suitable combination of transmit elements and receive elements. High voltage switch 410 switches the signal from the array to either the receive electronics 408 or the transmit electronics 406. The receive electronics 408 interface to a microprocessor or personal computer 402 having a memory 404 in a conventional manner. The transmit electronics also interface to the microprocessor or personal computer 402 in a conventional manner. The microprocessor 402 stores the identity of those piezels that provide a usable signal from the target 428. The array may be scanned in a regular fashion or in a random fashion to determine which piezels should be used. In one embodiment of the invention clusters of piezels may be used to boost signal strength. For example groups of piezels of predetermined number, such as 4, 9 or 16 piezels, are triggered to send out a pulse. The signal returned from the target is evaluated for clarity. If the signal is useable from a particular piezel the identity of the piezels is stored in memory 404. If the signal returned from the target is unusable, or has a relatively low signal to noise value, the piezel is deleted from this array/target combination because probably both transmit and receive capability is compromised simultaneously.

For example, during an echo cardiogram using a large array that may be an inch or two in one axis, some of the elements would be blocked by rib bones 426, 430. The signal from the blocked piezels would not be used to receive or transmit. In this example, since each element is a transmitter or receiver, the array could be constructed from DMOS. In one alternate embodiment of the invention some piezels may be phased differently to improve sensing of the target. The computer would select spatial location of the piezels used to sense the target and can additionally temporally adjust the send/receive waves so that they are optimized for best clarity.

Figure 17:
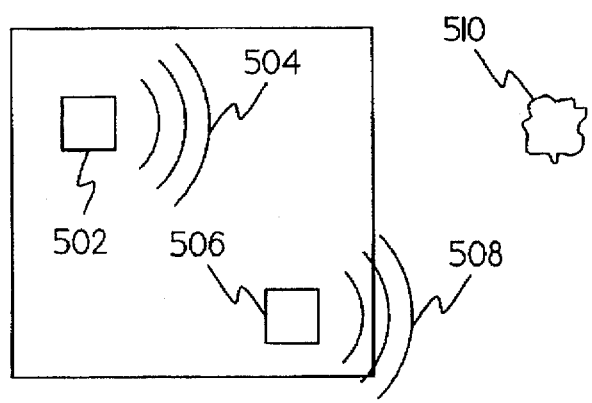
FIG. 17 shows an example of target imaging optimization in accordance with one aspect of the invention.
Figure 18:
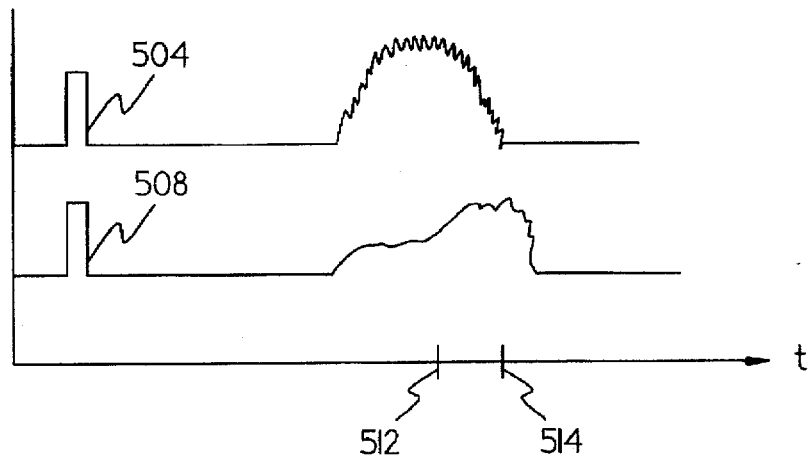
FIG. 18 shows phasing time information of typical piezels illustrated in FIG. 17.

Now referring to FIG. 17 where an example of target imaging optimization is shown. A first piezel 502 transmits a pulse 504. A second piezel 506, spatially separated from the first piezel 502, transmits a pulse 508. As shown in FIG. 18, first piezel 502 may best highlight target tissue 510 at time 512 and second piezel 506 may best highlight target tissue 510 at time 514. The computer 402 stores the preferred phasing time information of each piezel 502, 506 so that a composite picture from each piezel 502, 506 is made from the best temporal data. The computer optimizes an image by selecting piezels spatially, and associating a preferred phasing for each selected piezel.

Figure 19:
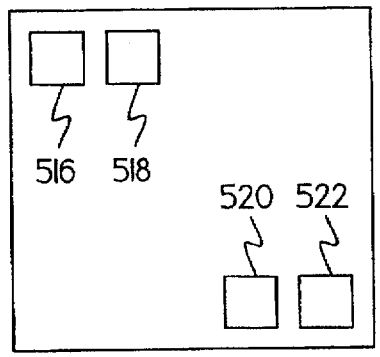
FIG. 19 illustrates transmit piezels having spatially associated receive and/or transmit piezels.

In one embodiment, the first piezel 502 and the second piezel 506 may each comprise a transmit and receive piezel. In an alternative embodiment, as shown in FIG. 19, each transmit piezel 516, 520 may have a spatially associated receive piezel 518, 522. For example, a checkerboard pattern of transmit piezels and receive piezels would provide for spatially associated transmit and receive elements. In both embodiments, the computer 402 stores the preferred phasing time between transmission and reception to provide for optimal phasing.

Figure 20:
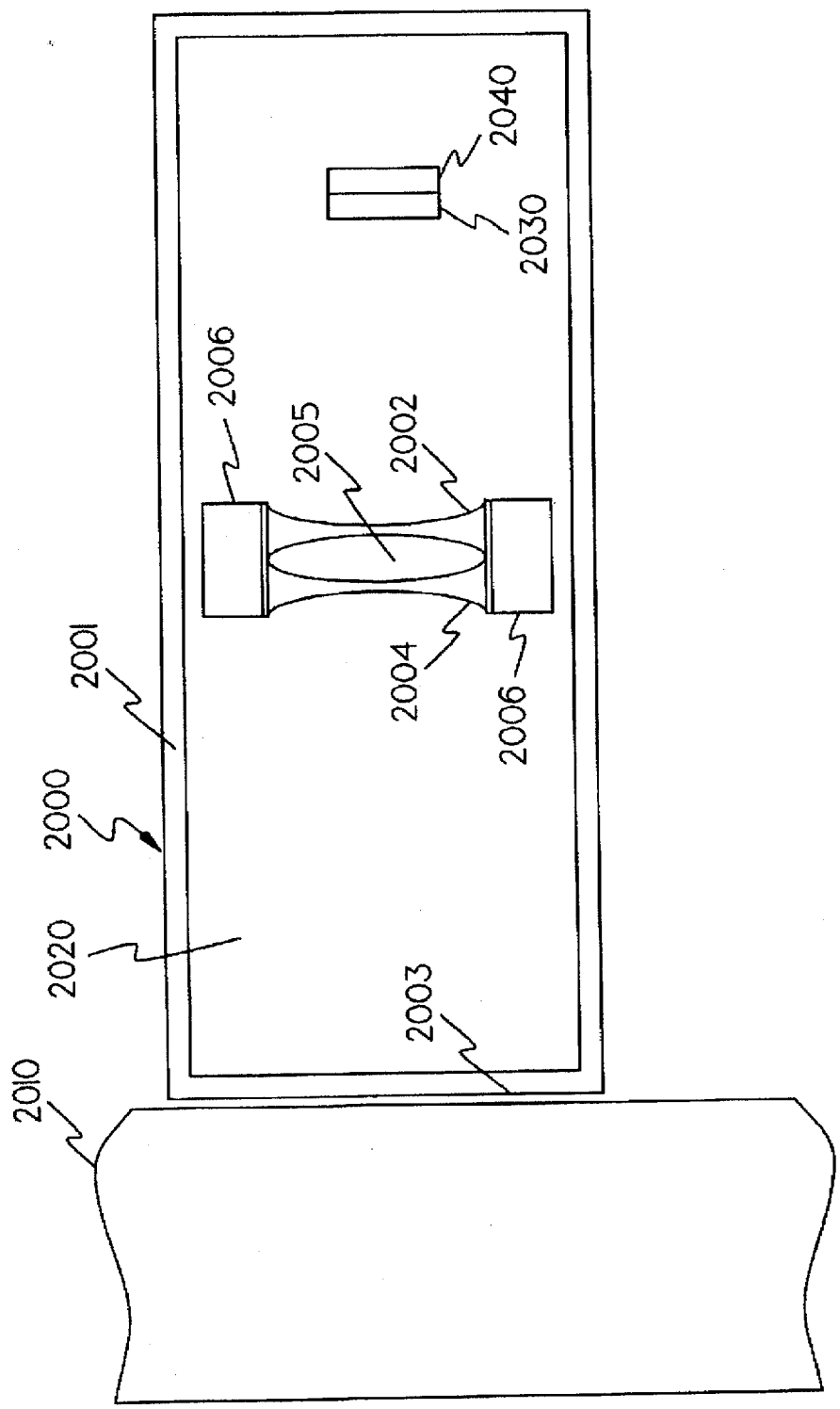
FIG. 20 schematically illustrates an overview of an ultrasonic system of the present invention employing a multi-element acoustic lens.

Now referring to FIG. 20, an overview of an ultrasonic system of the present invention employing a multi-element acoustic lens is schematically illustrated. The ultrasonic system 2000 includes a housing 2001, an ultrasonic window 2003, a multi-element lens 2005, piezoelectric material 2030, silicon integrated circuit 2040 and optional transmit transducers 2006.

In operation, the ultrasonic window 2003 may be in contact with, for example, body tissue 2010. The multi-element acoustic lens may comprise at least two lenses 2002, 2004 where lenses 2002, 2004 may be constructed as discussed hereinabove with reference to FIG. 14, for example. Piezoelectric material 2030 may be constructed as one of the ultrasonic arrays as described herein. Optional transmit transducers 2006 may be of conventional design or be constructed in accordance with an embodiment of the apparatus of the present invention as described hereinabove. The housing 2001 may advantageously be filled with a known ultrasound coupling fluid 2020 or equivalent. Piezoelectric material 2030 and silicon integrated circuit 2040 are electrically connected as described herein with, for example, bump bonding techniques.

FIG. 21 schematically illustrates one embodiment of an analog-to-digital converter constructed on an integrated circuit 2100 employed in one aspect of the invention. The integrated circuit 2100 comprises a plurality of similarly constructed unit cells 2112, an analog-to-digital converter (ADC) 2120, a buffer 2122 and a multiplexer 2124. In one useful embodiment, 64 such unit cells may be constructed on a silicon die of about 12 mm by 10 mm.

Each unit cell 2112 may comprise a bump 2104 for connection to an ultrasonic transducer array, a sample-and-hold circuit 2110, a shift register 2108, a variable gain preamplifier 2102 and an output 2106. The elements are connected and operate according to conventional integrated circuit design rules. Each unit cell output 2106 is coupled to an on-chip ADC for converting analog signals representing ultrasonic energy to digital signals for further processing In one useful embodiment, the on-chip ADC 2120 may comprise a 10 bit, 5 microsecond/sample ADC. The ADC 2120 is coupled to a buffer such as, for example, a first-in-first-out (FIFO) buffer 2122. Buffer 2122 is coupled to a multiplexer 2124 that provides an output 2126 to external processing circuitry. In one example embodiment of the invention the multiplexer output may be a 10 bit parallel output.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An ultrasonic array comprising:
   (a) a plurality of ultrasonic transducers, each of the plurality of ultrasonic transducers having a matching layer/common electrode end and a driving layer/individually isolated end;
   (b) a means for bump bonding each one of the plurality of ultrasonic transducers to a substrate;
   (c) a high voltage electrical conductor connected to at least one driving layer/individually isolated end to provide a drive signal to at least one of the plurality of ultrasonic transducers;
   (d) a conductive layer disposed to electrically connect each matching layer end; and
   (e) an outer matching layer connected to the conductive layer wherein the bump bonding means is constructed of a size so as to provide mechanical stability while reducing cross talk among the plurality of ultrasonic transducers.

2. The apparatus of claim 1 wherein the means for bump bonding each one of the plurality of ultrasonic transducers to a substrate further comprises an indium bump or solder bump bond wherein the indium bump or solder bump bond comprises an area in contact with an ultrasonic transducer of less than 20 percent of the driving layer/individually isolated end for the ultrasonic transducer.

3. The apparatus of claim 1 wherein the substrate further comprises a semiconductor.

4. The apparatus of claim 1 wherein the plurality of ultrasonic transducers further comprise a piezoelectric element.

5. The apparatus of claim 1 wherein the plurality of ultrasonic transducers further comprise an array of receivers.

6. The apparatus of claim 1 wherein the plurality of ultrasonic transducers further comprise an array of transmitters.

7. The apparatus of claim 1 wherein the plurality of ultrasonic transducers further comprise at least one transmitter.

8. The apparatus of claim 1 wherein the plurality of ultrasonic transducers further comprise a plurality of transmitters arranged in a predetermined pattern.

9. The apparatus of claim 8 wherein the predetermined pattern is selected from the group consisting of a rectangular pattern, a circular pattern, a reticulated pattern, a diagonal pattern, a grid pattern, a random pattern, a triangular pattern, a cross pattern and an oval pattern.

10. The apparatus of claim 8 wherein the plurality of transmitters are connected with a plurality of high voltage electrical conductors.

11. The apparatus of claim 1 wherein the means for bonding has a predetermined size that is small relative to the size of an ultrasonic transducer.

12. The apparatus of claim 1 wherein the means for bonding comprises an indium bump bond connected to a stepped or sloped conductor potted in an acoustic matching medium.

13. The apparatus of claim 1 wherein one matching layer comprises stepped or sloped layers on at least one surface and the outer matching layer comprises stepped layers on at least one surface.

14. The apparatus of claim 1 further comprising an acoustic lens located in an acoustic medium or fluid between a source of ultrasonic energy of a predetermined wavelength and the plurality of ultrasonic transducers wherein the acoustic lens is constructed so as to provide a gradual transition from one medium or fluid to another.

15. The apparatus of claim 14 wherein the acoustic lens has a surface shaped as a binary concave lens.

16. The apparatus of claim 14 wherein the acoustic lens comprises a graded surface area having gradations less than the predetermined wavelength.

17. The apparatus of claim 1 wherein the conductive layer further comprises a plurality of isolated conductive matching layer tiles.

18. The apparatus of claim 1 wherein the plurality of ultrasonic transducers further comprise a plurality of receivers arranged in a predetermined pattern.

19. The apparatus of claim 18 wherein the means for bump bonding each one of the plurality of ultrasonic transducers to a substrate further comprises an indium bump or solder bump bond wherein the indium bump or solder bump bond comprises an area in contact with an ultrasonic transducer in the range of 10 percent to 5 percent of the driving layer/individually isolated end for the ultrasonic transducer.

20. The apparatus of claim 1 wherein the matching layer/common electrode end further comprises a lossy matching layer so as to further reduce cross talk.

21. An adaptive ultrasound array comprising:
   (a) an array of ultrasonic transducers having a first plurality of receivers and a second plurality of transmitters having a signal;
   (b) means for switching each one of the first plurality of receivers and each one of the second plurality of transmitters connected to the signal having a receive signal and a transmit signal; and
   (c) means for scanning the array of ultrasonic transducers to select at least one receiver from the plurality of receivers and to select at least one transmitter from the plurality of transmitters that provide a useable signal having a signal to noise ratio above a predetermined value; and (d) means for processing the receive signal and transmit signal from the at least one selected receiver and the at least one transmitter to adaptively process the receive signal and transmit signal.

22. The apparatus of claim 21 wherein the means for processing the receive signal and transmit signal further comprises a microprocessor.

23. The apparatus of claim 21 wherein the means for processing the receive signal and transmit signal further comprises a personal computer.

24. A method for operating an adaptive ultrasonic array comprising the steps of:

(a) transmitting an ultrasonic pulse from the adaptive ultrasonic array to a target;

(b) receiving a first peak return pulse from the target with the adaptive ultrasonic array;

(c) receiving a second peak return pulse from the target with the adaptive ultrasonic array and noting a time of the second peak return pulse; and (d) adjusting imaging of the target with the adaptive ultrasonic array with the time of the first peak return pulse and the time of the second peak return pulse.

25. An ultrasonic system comprising:

(a) a housing filled with a known ultrasound coupling fluid;

b) an ultrasonic window mounted at a first end of the housing;

c) a multi-element acoustic lens mounted within the housing and located to receive energy from the ultrasonic window;

d) piezoelectric material; and e) an integrated circuit wherein the piezoelectric material and silicon integrated circuit are electrically connected by a bump bonding means for electrical connection, wherein the bump bonding means is constructed so as to provide mechanical stability while reducing cross talk among the plurality of ultrasonic transducers.

26. The ultrasonic system of claim 25 wherein the integrated circuit comprises:

(a) a plurality of unit cells each having a unit cell output;

(b) a plurality of analog-to-digital converters (ADCs) each having an input connected to a unit cell output and each having an ADC output; and (c) means for multiplexing coupled to the ADC output.

27. The ultrasonic system of claim 25 wherein a unit cell comprises:

(a) a bump means for connection to an ultrasonic transducer array;

(b) sample-and-hold circuits connected to receive signals through the bump means;

(c) a shift register connected to the sample-and-hold circuit; and (d) a variable gain preamplifier connected to amplify signals received through the bump means.

28. The ultrasonic system of claim 25 wherein the multi-element acoustic lens comprises at least two lenses where the each of the at least two lenses comprises a graded surface area having gradations less than the predetermined wavelength.

\* \* \* \* \*

UNITED STATES PATENT AND TRADEMARK OFFICE
CERTIFICATE OF CORRECTION

PATENT NO. : 5,732,706
DATED : March 31, 1998
INVENTOR(S) : White et al.

It is certified that error appears in the above-identified patent and that said Letters Patent is hereby corrected as shown below:

Column 3, line 3, after the word "and" insert --49--.

Signed and Sealed this

Fifteenth Day of September, 1998

Attest:

BRUCE LEHMAN

*Attesting Officer*                *Commissioner of Patents and Trademarks*